United States Patent
Schultheis et al.

(10) Patent No.: US 12,007,096 B2
(45) Date of Patent: Jun. 11, 2024

(54) ILLUMINATION SYSTEMS WITH OPTICAL WAVEGUIDE HAVING DIFFUSER ELEMENTS

(71) Applicant: SCHOTT AG, Mainz (DE)

(72) Inventors: Bernd Schultheis, Schwabenheim (DE); Christian Henn, Frei-Laubersheim (DE); Tobias Klink, Ruesselsheim (DE); Oliver Keiper, Huenstetten (DE); Hubertus Russert, Jugenheim (DE)

(73) Assignee: SCHOTT AG, Mainz (DE)

( * ) Notice: Subject to any disclaimer, the term of this patent is extended or adjusted under 35 U.S.C. 154(b) by 0 days.

(21) Appl. No.: 17/841,604

(22) Filed: Jun. 15, 2022

(65) Prior Publication Data

US 2022/0397262 A1 Dec. 15, 2022

(30) Foreign Application Priority Data

Jun. 15, 2021 (DE) ...................... 10 2021 115 485.5

(51) Int. Cl.
*F21V 13/04* (2006.01)
*F21V 3/06* (2018.01)
(Continued)

(52) U.S. Cl.
CPC ............ *F21V 13/04* (2013.01); *F21V 3/0615* (2018.02); *F21V 7/0066* (2013.01); *G02B 6/001* (2013.01);
(Continued)

(58) Field of Classification Search
CPC ...... F21V 13/04; F21V 3/0615; F21V 7/0066; G02B 6/001; G02B 6/02; G02B 6/241
See application file for complete search history.

(56) References Cited

U.S. PATENT DOCUMENTS

| 4,466,697 A | 8/1984 | Daniel |
| 5,871,521 A | 2/1999 | Kaneda |

(Continued)

FOREIGN PATENT DOCUMENTS

| DE | 10129029 | 12/2002 |
| DE | 102015119875 | 12/2016 |

(Continued)

OTHER PUBLICATIONS

Hasan, "Photodynamic Therapy of Cancer", Cancer Medicine, 2003, pp. 605-622.

(Continued)

*Primary Examiner* — Christopher E Dunay
(74) *Attorney, Agent, or Firm* — Ruggiero McAllister & McMahon LLC (57) ABSTRACT

An illumination system for a medical technology therapy and/or diagnosis system is provided. The system includes a light source, an optical waveguide, and an optical element in the form of a diffuser element. The optical waveguide has a first end that is connectable or assignable to the light source and the diffuser element is arranged at a second end of the optical waveguide so that light from the optical waveguide is injected into the optical element. The optical element has a lateral surface covered by a reflector layer at least in a section thereof. The reflector layer includes a mirror layer. The optical element has a light-reflecting area covered by the reflector layer and a light-transmissive area that is free of the reflector layer. Thus, light injected into the optical element is reflected on the light-reflecting area and emitted from the light-transmissive area.

20 Claims, 3 Drawing Sheets

(51) Int. Cl.
  *F21V 7/00* (2006.01)
  *F21V 8/00* (2006.01)
  *G02B 6/02* (2006.01)
  *G02B 6/24* (2006.01)
  *F21Y 115/10* (2016.01)

(52) U.S. Cl.
  CPC ............... *G02B 6/02* (2013.01); *G02B 6/241* (2013.01); *F21V 2200/13* (2015.01); *F21Y 2115/10* (2016.08)

(56) References Cited

U.S. PATENT DOCUMENTS

| | | | |
|---|---|---|---|
| 6,423,055 B1* | 7/2002 | Farr | A61B 18/245 606/7 |
| 6,810,184 B2 | 10/2004 | Skutnik | |
| 2005/0165462 A1* | 7/2005 | Bays | A61N 5/0601 607/88 |
| 2005/0273090 A1 | 12/2005 | Nieman | |
| 2006/0104593 A1* | 5/2006 | Gowda | A61N 5/062 385/139 |
| 2006/0217693 A1 | 9/2006 | Gowda | |
| 2009/0059359 A1* | 3/2009 | Nahm | A61B 5/0066 359/368 |
| 2009/0131931 A1* | 5/2009 | Lee | A61B 5/0084 606/41 |
| 2009/0204111 A1 | 8/2009 | Bissig | |
| 2009/0275931 A1 | 11/2009 | Markus | |
| 2014/0092620 A1* | 4/2014 | Tissot | G02B 6/0026 29/592.1 |
| 2016/0100750 A1 | 4/2016 | Furuta | |
| 2019/0159867 A1 | 5/2019 | Bruder | |
| 2020/0222712 A1 | 7/2020 | Schultheis | |
| 2020/0289202 A1 | 9/2020 | Miyagawa | |
| 2020/0405391 A1 | 12/2020 | Massimini | |
| 2022/0252776 A1* | 8/2022 | Stein | A61B 18/22 |

FOREIGN PATENT DOCUMENTS

| | | |
|---|---|---|
| EP | 3184885 | 6/2017 |
| WO | 2008024397 | 2/2008 |
| WO | 2017174549 | 10/2017 |
| WO | 2019063799 | 4/2019 |

OTHER PUBLICATIONS

"Laser-induced interstitial thermotherapy (LITT) for malignant tumors" An Assessment by the German Medical Association and the National Association of Statutory Health Insurance Physicians, Cologne, Jan. 18, 2002, inter alia. 122 pages.

Finlay, "In vivo determination of the absorption and scattering spectra of the human prostate during photodynamic therapy", Proc. SPIE Int. Soc. Opt. Eng. Jun. 14, 2014; 5315: p. 132-142.

* cited by examiner

ILLUMINATION SYSTEMS WITH OPTICAL WAVEGUIDE HAVING DIFFUSER ELEMENTS

CROSS REFERENCE TO RELATED APPLICATIONS

This application claims benefit under 35 USC § 119 of German Application DE 10 2021 115 485.5 filed Jun. 15, 2021, the entire contents of which are incorporated herein by reference.

BACKGROUND

1. Field of the Invention

The invention relates to an illumination system which comprises at least one light source, an optical waveguide, and an optical element which is preferably in the form of a diffuser element and is arranged at a distal end of the optical waveguide, so that light from the optical waveguide is injectable into the optical element.

2. Description of Related Art

Such illumination systems are increasingly being used in the medical sector. The following main fields of application can currently be classified: photodynamic therapy (PDT) or photoimmunotherapy (PIT) for tumor treatment; endovenous laser therapy (EVLT) for the treatment of varicose veins; laser-induced interstitial thermotherapy (LITT); and other applications, e.g. in the field of dental medicine, ophthalmology, and dermatology, or for the treatment of epilepsy.

Photodynamic therapy (PDT) is a minimally invasive therapy option for various types of cancer. PDT is a procedure for treating tumors and other tissue alterations (such as angiogenesis) using light in combination with a substance that can be activated by light. At the beginning of the treatment, light-sensitive substances, so-called photosensitizers, are injected intravenously into the bloodstream of the patient, which accumulate in or on the cancer cells. These natural photo-substances concentrate in the tumor cells, causing them to be highly sensitive to light. For this purpose, the tumor tissue is punctured using a plurality of cannulas (typically up to 8) during the PDT treatment, and in each one of them a light source has to be provided so as to be the best possible spatially distributed over the tumor tissue. Laser light, usually with wavelengths in the visible spectral range, for example green light with a wavelength of 532 nm or red light with a wavelength of 690 nm, illuminates the tumor tissue from the inside as evenly as possible, thereby generating aggressive oxygen radicals in these cells, which selectively destroy the tumor cells. In contrast to the diseased cells, healthy cells should remain unaffected by this chemical reaction. The exact mechanism of action is described in "Photodynamic Therapy of Cancer", Cancer Medicine, 2003, inter alia. In photoimmunotherapy (PIT), on the other hand, an appropriately modified photosensitizer is used to trigger an immune reaction on or in the cancer cell, which leads to the death of the cancer cell when exposed to light.

Regarding the light sources, a distinction is usually made between cylindrical diffusers and spot diffusers, which produce a forward-directed illumination cone, and point diffusers exhibiting radial light emission. In the case of cylindrical diffusers it is particularly important that lateral emission is as homogeneous as possible over the length of the diffusers in the operating state thereof. This means axially, i.e. emission intensity is consistent at all points along any line from the proximal end to the distal end in the direction of the longitudinal axis within the scope of homogeneity requirements, as well as radially, i.e. emission intensity is also consistent at all points along every circumferential line along the longitudinal axis within the scope of homogeneity requirements, so that the cylindrical diffusers are substantially effective as Lambertian radiators.

At the same time, it is also advantageous if a high scattering efficiency can be achieved in order to ensure the lowest possible heat input into the tissue, while forward-directed emission, in particular from the distal end, should be avoided. Laser output power for PDT applications is typically <5 W of continuous power, so that a maximum of between 100 mW and 1000 mW, typically between 200 mW and 500 mW is emitted per cm diffuser length.

Existing examples are diffuser elements made of a thin silicone cylinder in which scattering particles are embedded. Document DE 10129029 A1 describes a flexible device for thermal obliteration of biological tissue by laser radiation using an optical waveguide which carries the laser radiation and which has a distal end that is surrounded by a jacket which is transparent or opaque to the laser radiation and which projects beyond the fiber end. However, manufacture thereof with sufficient emission homogeneity is very complex and costly, since conglomerates of the scattering particles often form emission spots with an intensity significantly above the average.

In some applications, optical waveguides with the diffuser elements are only used once and are disposed of after each treatment. Therefore, there is also a certain cost pressure in terms of manufacturing costs. Accordingly, reusable solutions are increasingly being considered. Such solutions must then allow to be reconditioned in compliance with the relevant known standards, i.e. they have to be disinfectable and/or sterilizable. Preparation processes that can be mentioned here include in particular cleaning and disinfection processes with strongly alkaline solutions and sterilization by autoclaving at temperatures of up to 135° C. and typical steam pressures of about 3 bars. Typically, a few tens to several hundreds of such processing cycles are then assumed. This places high requirements on thermal, chemical, and also hydrolytic resistance.

In EVLT, the attending physician introduces a catheter into the affected vein via a tiny puncture site, which catheter serves as a guide rail for the vein laser. The inner wall of the vessel is then heated by lateral emission of the laser energy using the diffuser, which causes the vein to collapse and being sealed. Pathological reflux of the venous blood is prevented in this way. As a result, the vein hardens, regresses, and can be broken down by the body. Usually, so-called ring or double ring fire systems are used as the light source. For uniform treatment, the optical waveguide with the emitting element is often manually pulled through the vein section to be treated at the most constant speed possible, which makes application more difficult, since non-observance or excessive dwell time at one point can result in further cell damage.

LITT is a minimally invasive procedure that is used for local tumor destruction. The tumor is punctured under imaging control (e.g. sonography/MRI), one (or more) laser fiber(s) are introduced into the focus of the tumor, and scleroses is induced in the latter by thermal energy. In particular Nd:YAG lasers (1064 nm) and diffuser tip applicators are used in this case. Laser output power is about 5 to 8 W (cf. "Laserinduzierte Interstitielle Thermotherapie (LITT) bei malignen Tumoren" BÄK and KBV January 2002, inter alia).

A further, in particular volume-scattering diffuser is disclosed in EP 3,184,885 A1, for example, which describes a diffuser at the end of an optical fiber made of fused silica, and for producing the diffuser it is contemplated to apply a scattering mass on the distal fiber end of the optical fiber and to solidify it to form the diffuser. A drawback of such approaches is that such volume-scattering implementations imply a strongly exponential drop in intensity. Moreover, porous materials are not preferred in medical technology applications, in view to their reprocessability.

Document U.S. Pat. No. 6,810,184 B2 describes an approach in which nanoporous silica-clad optical fibers are used to make fibers having integrally formed diffusion tips that can be fused to other fibers. EP 2062077 A4, US 2009/0204111 A1, and DE 102015119875 A1 disclose diffusers which are produced by introducing structures into or applying structures onto the fiber using lasers.

WO 2008/024397 A2 discloses, inter alia, a diffuser for outputting optical energy of high power density to a treatment site at the distal end of at least one optical fiber. It is contemplated that the scattering centers are located in a predetermined length of the fiber core or in or near an interface between the fiber core and the cladding within this predetermined length.

However, in the approaches presented above, drawbacks that have to be expected in particular include that, with a sufficiently homogeneous implementation of the scattering centers, lateral radiation is not achieved with the degree of homogeneity required in the medical field due to the exponential drop in lateral emission or due to uneven distributions.

US 2009/0204111 A1 describes a laser delivery system comprising an optical fiber having a core and a cladding layer that covers at least a portion of the core, wherein the cladding layer has a lower refractive index than the core; and a non-feature portion as well as a feature portion having features that force light to be emitted radially from the feature portion and provide a desired radial light output pattern. It is contemplated that the features are selected from the group consisting of helical structures, radial cuts, axial cuts, and a combination thereof.

DE 102015119875 A1 discloses an optical waveguide comprising a light wavelengths carrying core, an area in the optical waveguide with micro-modifications provided in the area of the optical waveguide, and with the micro-modifications arranged in an ordered fashion.

WO 2019/063799 A1 describes an illumination system, in particular for a medical technology therapy and/or diagnosis system, comprising at least one laser light source, an optical waveguide which can be connected to and/or associated with the at least one laser light source at a proximal end thereof, and comprising a diffuser element at the distal end of the optical waveguide, the diffuser element having a longitudinal axis extending perpendicular to the coupling surface of the optical waveguide into or in the diffuser element. The diffuser element emits light over its active length laterally of the longitudinal axis, with the diffuser element comprising at least one diffuser base body and the diffuser base body including at least one scattering element. The illumination system includes means for homogenizing the emission intensity along the longitudinal axis of the diffuser base body, and in its operating state, the illumination system exhibits an intensity distribution of lateral emission that deviates by not more than ±50%, preferably by not more than ±30%, and most preferably by not more than ±5% from the average lateral emission intensity. This allows to implement cylindrical diffusers that emit very homogeneously over their length, which moreover exhibit high efficiency and low self-heating, which is particularly advantageous for PIT and PDT applications.

As mentioned above, there are many applications in the field of medical technology where healthy tissue which usually directly adjoins the tissue to be irradiated might also be irradiated and thus damaged. The aim for the future is therefore to protect the tissue from undesired radiation.

SUMMARY

Therefore, the object of the invention is to enable improved irradiation of unhealthy tissue in a manner that meets the special requirements in a medical technology environment and, in particular, protects healthy tissue so that undesired physical damage to individuals is avoided.

Accordingly, the invention relates to an illumination system for a medical technology therapy and/or diagnosis system, in particular for use on living tissue, which comprises at least one light source, an optical waveguide which is connectable or assignable to the light source at a proximal end thereof, and an optical element preferably in the form of a diffuser element and arranged at a distal end of the optical waveguide so that light from the optical waveguide can be injected into the optical element. In the context of the invention, diffuser element is understood to mean a light-scattering body, in particular a body which conducts light and is able to preferably emit light in different directions. The light can be radiated in a diffuse or in a directed manner, in particular in a direction transversely, diagonally, perpendicular or parallel to the direction in which the light is injected into the optical element.

On one side, the optical element has a light-reflecting area and on the other side it has a light-transmissive area, with the light-reflecting area exhibiting at least partial reflectivity, and the light-transmissive area exhibiting at least partial transmittance, in particular high spectral transmittance, preferably up to a wavelength of about 2.5 µm. Light injected into the optical element can at least partially be reflected at the light-reflecting area. The reflection may be diffuse or directional. Within the light-transmissive area, light can be at least partially emitted from the optical element, in particular the aforementioned reflected light. The light-reflecting area in particular exhibits a higher reflectance than the light-transmissive area. Most preferably, the reflectance of the light-reflecting area is higher than that of the light-transmissive area by at least 30 percentage points, in particular at least 50, in particular at least 70 percentage points. For this purpose, the optical element is preferably covered with at least one reflector layer, at least in a section thereof, in particular it is covered with a reflector layer in the portion of the light-reflecting area, in order to impart at least partial reflectivity to the light-reflecting area. The optical element preferably remains free of the reflector layer at least in sections thereof, in particular it remains free of the reflector layer in the portion of the light-transmissive area, in order to impart at least partial transmittance to the light-transmissive area. The reflector layer may cover a surface and/or lateral surface of the optical element. Furthermore, the reflector layer may comprise a mirror layer or may be in the form of a mirror layer.

Accordingly, the optical element may have a lateral surface that is covered by a light-reflecting reflector layer, at least in a section thereof, which reflector layer preferably includes a mirror layer, so the optical element comprises a light-reflecting area that is covered by the reflector layer, and comprises a light-transmissive area which preferably remains free of the reflector layer, so that the light to be emitted by the optical element can at least partially be reflected and light can be emitted from the light-transmissive area. Thus, light can selectively be emitted from the light-transmissive area. The term lateral surface is in particular understood to mean a surface of the optical element.

Most preferably, the reflectance of the reflector layer is greater than 90% for at least one wavelength range. The reflector layer may also be in the form of a mirror layer.

The range of wavelengths for which the reflector layer is designed may preferably encompass the visible spectral range (VIS) between about 400 nm and about 700 nm, for example in particular between 400 nm and 450 nm or between 600 nm and 700 nm, and also the infrared range (IR) between about 700 nm and about 2.5 µm, in particular the near infrared range (NIR) between about 700 nm and about 1200 nm, e.g. 980 nm or 1064 nm. Wavelengths in the near UV range between about 350 nm and about 400 nm are also conceivable.

However, the light-transmissive area or the light-reflecting area can also be designed such that a predefinable wavelength range or a predefinable main wavelength is transmitted or reflected. Preferably, this predefinable range is not exceeded by more than 20 nm, more preferably by not more than 10 nm, most preferably by not more than 5 nm. Such a predefinable range may, for example, include wavelengths of a specific color, in particular green or red.

What can advantageously be achieved by the fact that the optical element has an at least partially light-reflecting area on one side and an at least partially light-transmissive area on the other side, with the light-reflecting area exhibiting higher reflectance than the light-transmissive area, is that light emission from the light-reflecting area is reduced or avoided, while light emission from the light-transmissive area is increased or limited thereto. This advantageously provides for a more targeted emission of light, in particular in order to irradiate diseased tissue and at the same time protect adjoining healthy tissue.

In particular due to the fact that the reflector layer is applied to the diffuser element only in sections thereof, the light will be selectively emitted from non-covered areas, which means, for example, that during medical treatment only diseased tissue or tissue to be irradiated can be selectively irradiated, for example tissue is selectively sclerosed by application of energy, for example during an LITT application. Adjoining healthy tissue will be protected from irradiation in this way and will ideally not be damaged.

In one embodiment, the light can be radiated or emitted transversely to a longitudinal axis of the optical element and laterally over an active length of the optical element. If the optical element is in the form of an optical waveguide, it can advantageously carry or conduct light in a predetermined direction, for example along the longitudinal axis. In the context of the present disclosure, lateral emission is understood to mean emission that has directional components running in the radial direction, emanating from the longitudinal axis of the diffuser element. Lateral radiation intensity refers to the intensity of this radiation.

The geometry of emission can be adjusted by a corresponding geometric adjustment of the reflector layer, so that, for example, strip-like or lens-shaped patterns can be projected onto the tissue surface to be treated. Hence, it is advantageous if at least one area of the diffuser element that is uncovered by the reflector layer, for example an opening in the reflector layer, extends along the longitudinal extension of the diffuser element and this non-covered area is light-transmissive, so that light conducted through the diffuser element can be emitted in a strip-like shape, in particular in linear form. The light-transmissive area may extend linearly or non-linearly in this case. A linear emission area allows for sectional emission, so that the tissue to be irradiated will not be irradiated in a punctiform manner, but can be irradiated over a larger area, and at the same time this area can be kept within defined limits in order to protect surrounding tissue.

By appropriate geometrical adjustment of the reflector layer, optionally also in combination with the geometry of the optical element itself, it is even possible to obtain more complex emission geometries. For example, gradual areas are also possible, in which case the reflector layer can be weaker in a defined area, in particular with lower reflectance than in a strongly reflecting area. However, geometries in which, for example, a light-transmissive, in particular strip-like area widens or narrows in one direction, for example in a longitudinal direction, are conceivable as well. In this case, a strip-like, lens-shaped, or oval area may extend longitudinally, transversely and/or diagonally relative to the longitudinal axis of the optical element, for example.

Ideally, the diffuser element is elongated or rod-shaped, so that it can be introduced into a catheter, for example. Furthermore, the diffuser element may have a substantially circular, oval, or polygonal cross-sectional shape, for example a hexagonal, rectangular, or square shape, and star-like shapes can also be implemented. In these cases, the light is preferably emitted laterally, via the facets or radial surfaces. Accordingly, a reflector layer that is applied to the diffuser element only in sections thereof or on some facets therefore makes it possible to emit light laterally only in a specific direction or in a predefined section. Particularly advantageously, at least one or more facets have a lenticular shape, preferably the shape of a Fresnel lens, so that the light can be focused and in particular allows for a more intensive irradiation or higher energy irradiation.

As described above, the diffuser element and/or optical element preferably has an elongated, rod-shaped or cylindrical shape, so that the diffuser element and/or optical element defines a longitudinal axis. The lateral surface is thus preferably a lateral surface extending around the longitudinal axis. In particular, the normal vector of the lateral surface is therefore perpendicular to the longitudinal axis.

It can be envisaged that the light-reflecting area of the optical element and/or of the diffuser element, which is covered by the reflector layer as described, extends at least over a particular angular range (e.g. over at least 90° or 180° or 270°) tangentially to the longitudinal axis, and that the light-transmissive area which, as described above, preferably remains free of the reflector layer, also extends at least over a particular angular range (e.g. over at least 1° or 10° or 20°) tangentially to the longitudinal axis. The light-transmissive area can thus be defined as a pie-shaped portion of the lateral surface, for example, but may of course also have more complex geometries, as already mentioned above.

The reflector layer is applied in particular concentrically on at least part of the lateral surface or on at least one facet. The reflector layer is preferably designed such that light from the diffuser element can be reflected back into the matrix of the diffuser element and/or light coming from outside is reflected back to the outside. This also means that the reflector layer may only be reflective on one side, so that light coming from outside can be introduced into the diffuser element, i.e. that the reflector layer is transmissive for light from outside. The reflector layer and/or the mirror layer may accordingly be designed as a dichroic mirror, for example as a short-pass, long-pass, narrow-band or broadband mirror.

Preferably, maximum reflectance is greater than 95% and most preferably greater than 99%, in particular for perpendicular incidence of light to the reflector layer, and the reflectance is selectively adjustable to a predefined wavelength of the employed light or in a predetermined range around a main wavelength of the light.

In an advantageous embodiment, the reflector layer exhibits a reflectance for a light incidence angle of greater than 45°, preferably greater than 60°, most preferably greater than 80° with respect to the perpendicular to the reflector layer, which is more than 50%, preferably 70%, most preferably 90% of the reflectance at perpendicular incidence of light, in particular in a range around a maximum of reflectance at perpendicular incidence of light. In other words, the reflectance can be greater than 50%, preferably greater than 70%, preferably greater than 90% in a range, in particular in an angular range around the maximum reflectance at perpendicular incidence of light, preferably in the previously specified angular range.

Preferably, light within a predefined wavelength range is conducted through the diffuser element. However, different wavelengths are reflected differently. Therefore, a reflector layer is used which advantageously exhibits particularly high reflectance for several wavelengths and/or for a large angular range, so that a plurality of reflection maxima or a wavelength-dependent broad maximum reflection plateau is obtained for the employed light and so that reflectance is high for the corresponding wavelengths, in particular greater than 90%, even for an oblique incidence of light.

Hence, the reflectance can be matched to the wavelengths and angles that are used. This allows to reflect a particularly large amount of light. This is particularly important because absorption of light should be avoided. Since the illumination system can be operated with output powers of up to 30 watts, typically between 10 W and 20 W, any absorption can lead to strong heating of the diffuser element and/or of the reflector layer. Such high absorption might cause damage to the illumination system, for example due to overheating, or in worse cases even injury of individuals. Therefore, the illumination system should be kept cold enough, through high reflection, so as to not being damaged during operation. In other words, self-heating of the optical element or of the diffuser element should be avoided, preferably by having a maximum quantity of light reflected.

It is also conceivable that the mirror layer in particular of the reflector layer includes or is made of a metallic layer, which preferably comprises one or more metals from the group of noble metals or a metal from the group consisting of Mg, Al, Cu. An alloy of these materials is also conceivable. Due to their high reflectance in a large wavelength range, noble metals such as Au, Pt, Pd, or Ag are preferably used. Also, their processability with regard to the producing of the reflector layer is comparatively simple. Due to the low oxidizing ability of Au, it is inert, for example to body fluids, and also exhibits low interaction with endogenous proteins, so that Au offers particularly good biocompatibility and is therefore preferred. Overall, the reflector layer should meet the requirements demanded in medicine, in particular standardized requirements in terms of biocompatibility and cytotoxicity.

As mentioned before, the lateral surface of the diffuser element or optical element is covered by a reflector layer, at least in a section thereof, which reflector layer preferably includes a mirror layer. In one embodiment, the reflector layer can comprise multiple layers and/or be in the form of a layer system. For example, the mirror layer of the reflector layer can consist of multiple layers in this case. However, a multi-layered reflector layer can also comprise one or more further layers which are provided in addition to the mirror layer, in particular disposed below and/or above the mirror layer. In the case of a multi-layered reflector layer or reflector layer system, i.e. comprising the mirror layer consisting of one or more layers and the further layers consisting of one or more layers, the preferred reflectance of the reflector layer as defined in more detail elsewhere relates to the entire reflector layer.

As an alternative or additionally, however, it is of course also possible that further layers not belonging to the reflector layer are provided below and/or above the reflector layer.

It may be contemplated for the reflector layer to be in the form of a layer system comprising at least one mirror layer and/or to have at least one of the following features: a base layer portion consisting of a single layer or a sequence of layers is provided below the reflector layer; at least one adhesion layer or adhesion promoting layer is provided between a diffuser base body and the mirror layer; on top of the diffuser base body, between the diffuser base body and the mirror layer, a layer portion is provided which has chemically and/or physically modified adhesion properties; the reflector layer comprises at least one passivation layer in an outward facing area, which at least partially covers the reflector layer.

In other words, a lateral surface reflector of the illumination system with its at least one reflector layer may come in the form of a layer system, and/or at least one adhesion layer or adhesion promoting layer may be provided between a diffuser base body, which is also referred to as a diffuser element, and the reflector layer, and/or a layer portion with chemically and/or physically modified adhesion properties may be provided on the diffuser body.

As mentioned above, the reflector layer can be multi-layered or in the form of a layer system in one embodiment, and in particular it can be envisaged for the reflector layer to comprise at least one further layer in addition to the mirror layer.

Accordingly, in addition to the mirror layer, the reflector layer may comprise a lower layer disposed below the mirror layer, and/or an upper layer disposed above the mirror layer, with the lower layer in particular consisting of one or more layers and the upper layer in particular consisting of one or more layers.

A lower layer disposed below the mirror layer is preferably in the form of an adhesion layer or adhesion-promoting layer.

A lower layer disposed below the mirror layer is preferably in the form of a layer portion on the diffuser base body, which has chemically and/or physically modified surface properties.

A lower layer disposed below the mirror layer is preferably in the form of a base layer portion consisting of a single layer or a sequence of layers. A base layer portion, e.g. a base layer portion disposed below the mirror layer and in particular forming part of the reflector layer, and/or a base layer portion provided below the reflector layer may accordingly comprise one or more layers deposited on the optical element. As an alternative or additionally, it may be contemplated for the base layer portion to comprise a near-surface zone of the optical element with a modified surface property, in particular exhibiting increased surface energy and/or an increased number of oxygen radicals, which is in particular produced or producible by a chemical and/or physical process for modifying at least one surface property of the optical element. The base layer portion, e.g. the base layer portion disposed below the mirror layer and in particular forming part of the reflector layer and/or the base layer portion provided below the reflector layer may in particular define the adhesion layer or adhesion promoting layer.

It is therefore possible for the reflector layer or mirror layer to be directly disposed on the diffuser element, i.e. in particular without an adhesion layer. In this case, the passivation layer may, but does not need to be provided on the reflector layer and/or the mirror layer. Thus, it can be envisaged to provide the diffuser element or the reflector layer either with and without an adhesion layer and/or passivation layer. The adhesion layer or the layer portion having modified adhesion properties provides for enhanced adhesion of the reflector layer on the optical element or on the diffuser element or on the diffuser base body. This is in particular advantageous with regard to the corrosion resistance of the reflector layer, for example if the illumination system is used repeatedly and the reflector layer must withstand complex cleaning and sterilization processes in which caustic acids and/or alkalis are employed. Improved adhesion is also advantageous with regard to abrasion resistance, since friction may arise when the illumination system is moved within a catheter, for example, and the reflector layer reliably adheres to the diffuser base body. However, it is also conceivable for the adhesion layer to be designed so as to make a positive contribution to the reflectance. In other words, it is intended that the material, the surface, and/or the crystal orientation of the adhesion layer is selected with regard to the properties of the optical element or the diffuser element such that at least a portion of the light or predetermined wavelengths are reflected.

It should therefore be noted that for a reflector layer which comprises one or more further layers in addition to the mirror layer, i.e. for example a base layer portion and/or a passivation layer, a preferred reflectance relates to the entire reflector layer. More particularly, layers applied on the optical element below the mirror layer and/or layers applied above the mirror layer can contribute to the reflectivity of the reflector layer. This in particular also applies to a near-surface zone of the optical element which is disposed below the mirror layer and which can be produced, for example, by chemical and/or physical processes, since such processes will cause an alteration in the material of the optical element within a near-surface zone of the optical element, which can therefore then form part of the reflector layer.

It may also be envisaged for the layer system to additionally have at least one passivation layer in the outer area, which completely covers the reflector layer. The passivation layer offers additional protection, for example against acids or other potentially corrosive media such as gases or liquids. In addition, the passivation layer can enhance the biocompatibility of the reflector layer with respect to substances of the biological body or to the material in which the illumination system is intended to be used, so that a patient to be treated can also be protected.

It is furthermore contemplated for the illumination system to have at least one of the following features: the lower layer, in particular the adhesion layer or adhesion promoting layer or the base layer portion, is in the form of a dielectric layer, and this dielectric layer preferably includes oxides, nitrides, or oxynitrides of at least one element from the group consisting of Si, Al, Ti, Zr, Hf, Y, Zn; the upper layer, in particular the passivation layer is in the form of a dielectric layer, and this dielectric layer preferably includes oxides, nitrides, or oxynitrides of at least one element from the group consisting of Si, Al, Ti, Zr, Hf, Y, Zn.

Such materials are particularly suitable as adhesion promoters, in particular for layers made of pure metals, for example on glass. Moreover, metal oxides and metal nitrites are very corrosion-resistant to chemical and/or mechanical loads, such as abrasion. In particular oxides of Ti and Zr exhibit little interaction with body fluids, which leads to high biocompatibility. Such substances are therefore particularly suitable as a passivation layer.

In an advantageous embodiment, the mirror layer or the reflector layer is in the form of a dielectric multilayer system which comprises a sequence of low refractive index and high refractive index metal oxides and/or metal nitrites. Such layer systems can be optimally adjusted or adapted to a large extent, especially with regard to their reflection properties, so that the design or the layer system, preferably the illumination system with the reflector layer, can be tuned to specific applications, and in particular the wavelength range to be reflected can be precisely adjusted.

According to a further embodiment it may furthermore be contemplated that the mirror layer or the reflector layer is in the form of a layer that includes scattering centers and may also be implemented in combination with reflector layers made of metals and/or dielectric layers, in which case the optionally additional reflector layers made of metals and/or dielectric layers will enclose the layer that includes the scattering centers on the outer surface, at least in some areas. Scattering elements in a specific concentration or with a specific layer thickness can in particular produce a reflective effect in a preferred direction. Generally, the reflecting effect will increase with increasing concentration of scattering centers and with the thickness of this layer that includes scattering centers. Examples of this are layers which include white color pigments or have defects embedded, at which the incident light is scattered. The optionally additional metallic and/or dielectric reflector layers can completely prevent light from passing through to the outside.

It is also advantageous if the reflector layer is in the form of a layer system made up of three, four or more layers. This allows to better match individual layers to one another, and in particular allows to very precisely set the wavelengths to be reflected. This advantageously also permits to adjust the reflectance, so that a particularly high reflectivity can be achieved for the light that is employed. In order to increase reflectance, it can also be envisaged to have the mirror layer embedded in a multi-layer system, in particular in a dielectric layer system.

It is also conceivable that the layer thicknesses of the layers are defined according to at least one of the following features: the adhesion layer has a thickness of more than 5 nm, preferably more than 30 nm, and/or of less than 3000 nm, preferably less than 300 nm, more preferably less than 150 nm; the mirror layer has a thickness of more than 10 nm, preferably more than 20 nm, more preferably more than 50 nm, and/or of less than 5000 nm, preferably less than 200 nm, more preferably less than 100 nm; the passivation layer has a thickness of more than 5 nm, preferably more than 100 nm, more preferably more than 150 nm, and/or of less than 5000 nm, preferably less than 500 nm, more preferably less than 250 nm.

The adhesion layer is formed with a small layer thickness such that it has the least possible, in particular minimal impact on the reflectance of the reflector layer. Thus, the mirror layer is formed with a thickness according to the specified values such that the transmittance of light is reduced to a minimum and at the same time as little material as possible has to be used overall. For example, the layer thickness of the mirror layer and/or of the reflector layer is adjusted such that wavelengths above 0.35 µm, preferably above 0.4 µm, preferably above 0.8 µm and/or below 2.5 µm, preferably below 1.6 preferably below 1.2 µm can be reflected. The layer thickness of the mirror layer and/or the reflector layer is also matched in particular to an application wavelength. Thus, the reflectivity can be adjusted as a function of the application wavelength.

If the application wavelength is 2 µm, for example, then the reflectivity will be optimized to a wavelength range between 1.9 µm and 2.1 µm or narrower, for example, for 690 nm to between 670 nm and 710 nm, for example. In other words, the reflectivity of the mirror layer and/or of the reflector layer is adjusted to a wavelength which deviates not more than 100 nm, preferably 50 nm, more preferably 20 nm from the application wavelength. The thickness of the passivation layer is chosen so as to ensure corrosion resistance.

Sensibly, the reflector layer as described above in various embodiment variants should exhibit an abrasion resistance or adhesion that should at least resist customary or standardized abrasion tests and adhesion tests. Such tests are very well suited to verify the mechanical or physical corrosion resistance. Furthermore, it can be ensured that the illumination system can be used in the intended environment, since strict regulations apply in the medical field.

Good adhesion and physical resistance to mechanical loads can be verified by a self-adhesive tape test, for example. In this case, a length of self-adhesive tape is applied to the coated optical element or to the reflector layer and is pulled off at a predefined angle. The test is passed if there is no coating on the self-adhesive tape after it has been pulled off and no delamination visible on the coating. In particular, attention has to be paid to ensure that the optionally provided passivation layer is also resistant to the mechanical loads mentioned.

The so-called rubber test is one type of a mechanical abrasion resistance test. In this case, a rubber or eraser is repeatedly moved back and forth on the layer to be tested with a specific force. The layer is considered to be abrasion-resistant if no damage can be found on the layer to be tested after this test cycle.

The passivation layer of the reflector layer may also be provided in the form of a barrier layer. Accordingly, it can be intended for the passivation layer to inhibit or block diffusion of polymer components into the reflector layer, in particular to or into the mirror layer, for example diffusion of acids and/or oxygen and in particular of ions of acidic or alkaline solutions. Accordingly, the passivation layer can delay or prevent permeation of, for example, acids, oxygen or other constituents of the air into the reflector layer.

In particular for processing medical products it is common to use alkaline cleaners or disinfectants (e.g. NEOD-ISHER with a pH of about 11). Furthermore, sterilization techniques are known which use ethylene oxide gas, which is in particular used for single-use items (disposables). Chemical resistance to this gas has to be ensure here as well. In additional, good hydrolytic resistance has to be ensured with regard to autoclaving processes (typically at 135° C./3 bar).

Furthermore, a rinsing solution containing sodium hypochlorite (NaClO) might be used, which is a bleaching agent or disinfectant, in which case the passivation layer should in particular be at least chemically resistant to such substances. This applies in particular to applications in the medical dental field.

Furthermore, the passivation layer or the reflector layer preferably has a hardness of, for example, at least 800 HV (Vickers hardness), preferably at least 1200 HV, most preferably at least 2000 HV, according to the customary or standardized test methods for determining the hardness of a layer. The passivation layer can thus also be in the form of a mechanical protective layer for the mirror layer or the reflector layer, in particular for a metallic mirror layer. In particular hard materials such as carbides or nitrides are protective due to their elevated hardness, such as AlN: up to approx. 2000 HV, $Si_3N_4$: up to approx. 2500 HV.

It is furthermore intended that the reflector layer is provided at the distal end of the diffuser element and/or at least partially encloses the diffuser element. It will be appreciated that a reflector layer applied to the distal end of the diffuser element can also have an adhesion layer and/or a passivation layer. The reflector layer can also be understood as a reflector surface, the reflector surface being in the form of sputter-deposited or vapor-deposited dielectric reflection layers on the distal end of the diffuser base body, consisting of a plurality of layers and matched in terms of reflectivity to the wavelength of the employed light, preferably exhibiting maximum reflectance at this wavelength. Ideally, the reflector surface is in the form of a directionally reflecting surface such as a metallic mirror surface with a metal coating in particular comprising Al, Ag, Au, or a diffusely reflecting surface, for example comprising a white paint layer, which reflects the light that passed through the diffuser base body back into it. This allows to at least partially compensate for or correct the usually exponential drop in intensity of the laterally emitted light along the diffuser base body. The amount of light that can be provided given a constant scattering rate is thus altered or is adjustable at least in sections, so that lateral emission can be homogenized.

Furthermore, sputter-deposited or vapor-deposited dielectric reflection layers have been found to be particularly advantageous on the distal end of the diffuser base body; they may consist of multiple layers and can be matched to the wavelength of the employed light in terms of reflectance, which means they may have a maximum at the wavelength to which they are matched. This allows to achieve ideal back reflection of the light injected during the operating state on the one hand, and on the other hand the avoidance of hotspots. Alternatively, it may as well be contemplated for the reflector to be implemented by a silver layer with rear passivation, which exhibits good broadband reflectivity. Such layers are particularly robust and capable of suppressing disturbing reflections which might lead to locally excessive intensities and also hotspots. This in particular allows to implement a very broadband reflector which has very good reflection properties both in the visible spectral range (VIS) and in the IR/MIR range, e.g. between 1 µm and 2.5 µm wavelength. Rear passivation prevents oxidation of the silver layer.

If the reflector surface is concave or convex, this allow to cause rays propagating almost parallel to the longitudinal axis to be at least partially reflected back at a steeper angle to the longitudinal axis so as to therefore be scattered more frequently at the scattering elements, so that the output efficiency of lateral emission is increased towards the distal end of the diffuser element, which implies a more homogeneous profile of emission intensity.

In an advantageous embodiment, the diffusor element has scattering elements that are enclosed in the matrix of the diffusor element, or the matrix of the diffusor element is enclosed by a material that contains scattering elements.

Scattering elements ensure that the light injected into the diffuser element is scattered or deflected in such a way that it can exit the diffuser element at the side, i.e. laterally. At least one scattering element is arranged along the entire longitudinal axis of the diffuser base body, with consistent cross section and essentially parallel thereto or, in the case of tapering diffuser base bodies, at an angle to the longitudinal axis. The scattering element may advantageously also be tubular and may in particular be arranged coaxially to the longitudinal axis. A plurality of scattering elements may be arranged in a specific predeterminable geometric arrangement around the longitudinal axis of the diffuser base body, preferably in a regular pattern, most preferably a circular pattern. A plurality of scattering elements that are arranged at an angle therefore preferably intersect at a vanishing point outside the diffuser base body.

According to a preferred implementation variant it is contemplated that the scattering elements in the diffuser base body are arranged in a radially evenly distributed pattern around the longitudinal axis of the diffuser base body, while a core zone around the longitudinal axis has no or a significantly reduced number of scattering elements per unit area compared to the number of scattering elements per unit area outside the core zone, so that the scattering elements are predominantly arranged outside this core zone within the matrix. This ensures that the injected light which is usually injected with a small NA (<0.3, typically about 0.2) will not immediately be scattered on the scattering elements. On the other hand, the core zone which is virtually free of scattering elements allows enough light to propagate to the distal end of the diffuser base body without being scattered. This allows to reduce the intensity near the injection site (proximal end of the diffuser base body) on the one hand, and on the other hand to increase the intensity near the distal end of the diffuser base body.

It is also conceivable that the diffuser element is structured at least partially or in sections in its volume and/or on its surface, or that the diffuser element has a colored or colorless, in particular transparent jacket, preferably made of colored glass or colored plastic. A texture on the surface of the diffuser element provides for improved adhesion of the reflector layer and/or improved scattering properties. A coating with boron nitride is an example of a coating or jacket which additionally supports a Lambertian emission characteristic and in this case in particular reduces a forward directed emission, in the direction of light injection. Other coatings of this type may consist of titanium oxide, calcium carbonate, or zirconium oxide, for example. The additional jacket may be in the form of a white glass tube, for example, which contains scattering elements in its glass matrix. However, a colorless or colored jacket is also conceivable.

According to one embodiment it is therefore suggested that the diffuser element with the reflector layer is enclosed, at least partially or in sections thereof, by a transparent or light-transmissive, colorless or colored jacket. The jacket typically has a diameter corresponding to 1.1 to 1.5 times the diameter of the diffuser element. The jacket is preferably defined by a rigid tube section made of glass or metal and/or by flexible tubing, in which case the tube section and/or tubing can preferably include further scattering centers and the jacket is at least partially made of one or more thin-walled heat-shrink tubes.

According to a particularly preferred implementation variant for the diffuser element it is proposed that the diffuser base body with the reflector surface as described above is provided with a transparent and/or translucent, dyed or colorless jacket enclosing it at least partially or in sections thereof. On the one hand, mechanical and/or chemical protection can be achieved in this way. On the other hand, the emission characteristic can moreover be further optimized with regard to homogeneity of the intensity of lateral emission by a suitable choice of materials, in particular if the latter contain scattering centers. This allows, for example, to support Lambertian light emission.

In a preferred implementation variant, the jacket is at least partially made of one or more thin-walled heat-shrink tubes. On the one hand, such heat-shrink tubes may cause an additional diffuse scattering effect and thus promote Lambertian emission. On the other hand, mechanical protection can be achieved in this way and can prevent possible chipping for the case the diffuser should be damaged. For example a thin-walled heat-shrink tube made of white dyed PET with a wall thickness of about 5 to 15 μm has proven to be suitable for this purpose. In order to suppress reflections, a thin-walled black or colored heat-shrink tube may additionally be provided partially. The coloring may be selected such that the application wavelength is absorbed particularly well. Such heat-shrink tubes are moreover implemented so as to be biocompatible. In this way, damage to individuals in the vicinity or in direct contact with the illumination system can be avoided. However, it is also possible for the jacket to come in the form of a sizing which preferably includes polyamide (PA), polyimide (PI), or polymethyl methacrylate (PMMA), or wax, wax-like components, or alkylsilane or can be made from at least one of these materials.

The diffuser base body may comprise or consist of a matrix made of transparent plastics material, in particular for improved processing, of glass, fused silica, or of transparent glass ceramics, and the scattering elements comprise or consist of: porous or pigmented or dyed plastics in the case of a matrix made of plastics material; pores, particles, porous or pigmented or dyed or inhomogeneities-containing glass or glass ceramics or glass ceramic elements and the crystallites contained therein in the case of a glass matrix; pores, porous fused silica, or ceramic or polycrystalline particles in the case of a fused silica matrix; pores, particles, porous or pigmented or dyed or inhomogeneities-containing glass or glass ceramics or glass ceramic elements and the crystallites contained therein in the case of a transparent glass ceramic matrix; or a combination of the respective scattering elements.

The inhomogeneities of the glass or the glass ceramic, which define the scattering elements in the case of glass or glass ceramic matrix implementations, comprise phase separation, segregations and/or incorporated particulates, seeds, and/or crystallites, and the scattering effect is selectively adjustable by a temperature-time process. The concentration of the scattering elements in the scattering area should be from 10 ppm to 1000 ppm and preferably from 20 ppm to 100 ppm. Here, the concentration value in ppm refers to the proportion of scattering particles in relation to the mass fractions of the constituents of the respective material, in particular the plastic material, the glass matrix, or the fused silica matrix in which the scattering particles are embedded. The respective scattering elements defined thereby, i.e. the pores, particles, porous or pigmented or, for example, white dyed or inhomogeneities-containing glass or glass ceramic elements and the crystallites contained therein preferably have a diameter from 10 nm to 1000 nm, most preferably from 100 nm to 800 nm.

It is furthermore advantageous if the diffuser element comprises borosilicate glass, phosphate crown glass, lead silicate glass, tin silicate glass, or alkali zinc glass and/or if the scattering elements comprise white glass rods, in particular enclosed by a jacket tube preferably made of borosilicate glass. This has the advantage that the diffuser base body as a whole can be visualized in X-ray imaging at least in part or sections thereof, so that the location of the diffuser in a patient's body can be determined. With regard to application wavelengths from 0.8 µm to about 2.2 µm, for example for the EVLT applications mentioned in the introductory part, it is also possible to use special IR-transparent glasses such as a phosphate crown glass, or a lead silicate glass.

With an approach based on fused silica it is in particular possible to address applications in the UV and/or IR range up to about 2.5 µm wavelength, if the fused silica has particularly few OH groups. Another advantage that can be mentioned here is the extremely high thermal resistance and the very low intrinsic absorption of fused silica, which in particular allows for an elevated laser output power of up to 50 W during application. In addition to scattering elements made of porous fused silica, it is also possible to use scattering elements made from or comprising ceramic pigments such as titanium dioxide, zirconium oxide, or aluminum oxide. Diffuser base bodies based on fused silica can be spliced particularly well to optical waveguides made of fused silica fibers, the fused silica fibers consisting of a core and a cladding which differ slightly in their refractive indices. The cladding may also be made of organic materials such as fluoroplastics, PMMA, or polyimide.

Glass ceramic-based implementations for the diffuser base body and/or the scattering elements may be made from a transparent aluminosilicate high-quartz solid solution glass ceramic, which is extremely thermal shock resistant and exhibits high spectral transmittance up to about 2.5 µm. Suitable scattering elements include, for example, a keatite glass ceramic which can be produced from the high-quartz solid solution glass ceramic by a suitable heat treatment process. Furthermore, cordierite glass ceramics or magnesium aluminum silicate glass ceramics are suitable as diffuser base bodies and/or scattering elements. A diffuser base body that is particularly preferred with regard to its manufacturing process is resulting when the diffuser base body is fabricated from fiber-optic rods made of borosilicate glass rods, tin silicate glass rods, or alkali zinc silicate glass rods, and/or when the scattering elements are made from white glass rods, preferably enclosed by a jacket tube made of borosilicate glass, tin silicate glass, or alkali zinc silicate glass to form the preform.

In one refinement of the invention, both the diffuser base body and the jacket tube may be made of the same type of glass. The refractive index of the jacket tube is preferably not greater than that of the matrix glass, and most preferably the two refractive indices are equal. This promotes the emission of the light scattered in the diffuser. This provides for cost-effective processes for the fabrication of diffusers, which allow to obtain such diffusers in virtually any length with a homogeneous emission intensity.

The invention also relates to a method for producing an illumination system for a medical technology therapy and/or diagnosis system, in particular for use on living tissue, which comprises at least one light source, an optical waveguide which is connectable or assignable to the light source at a proximal end thereof, and an optical element preferably in the form of a diffuser element and arranged at a distal end of the optical waveguide. Light from the optical waveguide can be injected into the optical element, and the method comprises the steps of: providing the diffuser element with a lateral surface; covering at least part of the lateral surface with a light-reflecting reflector layer which preferably comprises a mirror layer, so that the optical element comprises a light-reflecting area that is covered by the reflector layer and a light-transmissive area which remains free of the reflector layer, so that the light to be emitted by the optical element can be at least partially reflected and light can be selectively emitted from the light-transmissive area. The reflector layer exhibits a reflectance of more than 90% for at least one wavelength range.

Ideally, the illumination system covered by the reflector layer has at least one and preferably several of the properties or features described above in order to generate the respective advantages. The reflector layer preferably extends in the axial direction, in particular in the direction of the longitudinal axis of the optical element. The lateral surface can also be considered as a lateral surface layer or base layer portion, with a wall thickness preferably in the range from 1 to 100 µm.

It is also advantageous if the lateral surface is pre-treated or activated by creating a base layer portion with at least one altered surface property, in particular by chemical or physical processes, in order to change the surface properties of the lateral surface, so that the lateral surface can also be understood as a lateral surface layer or base layer portion, with a wall thickness preferably in the range from 1 to 100 µm. Accordingly, the reflector layer can be applied directly onto the lateral surface which in particular is not pre-treated, or onto the lateral surface layer or base layer portion.

The base layer portion may comprise a near-surface zone of the lateral surface which exhibits at least one altered surface property, in particular increased surface energy and/or an increased number of oxygen radicals, which ensure good adhesion of subsequent coatings, for example of the adhesion layer and/or the reflector layer. Such a near-surface sub-layer of the lateral surface layer is producible or can be produced by chemical or physical processes, for example, in order to change the surface properties of the lateral surface or lateral surface layer, in particular by a plasma treatment (e.g. low-pressure plasma or atmospheric plasma), UV treatment, arc (corona) discharge, and/or by chemical treatment such as by alkaline cleaners in an ultrasonic bath, or by a combination of such processes. Plasmas can also be employed to remove fats, oils or similar residues, and additionally to activate oxygen radicals. In other words, the base layer portion or a lowermost layer of the base layer portion may be defined by a radial portion of the outer lateral layer encompassing the outer surface thereof. Thus, the base layer portion may also consist of a single layer, for example, and this single layer is defined by chemical or physical processes with regard to surface properties on the basis of the outer lateral surface of the optical element.

However, the base layer portion may also consist of a sequence of layers, with the lowermost layer of the base layer portion being defined by chemical or physical processes with regard to surface properties on the basis of the outer lateral surface of the optical element, and with further layers disposed on this lowermost layer.

It is also conceivable for the reflector layer to be applied to the lateral surface in particular by using cathode sputter deposition, high-frequency sputter deposition, reactive sputter deposition, magnetron sputter deposition, vapor deposition, in particular ion beam vapor deposition, and/or thermal vapor deposition. Besides the techniques mentioned, the producing of at least one layer, preferably a plurality of layers of the reflector layer can in particular also encompass other coating techniques, for example vacuum processes, e.g. ion beam or thermal vapor deposition, chemical vapor deposition (CVD, e.g. PECVD, especially PICVD). Further coating techniques that are eligible for depositing one or more layers of the reflector layer include processes from a liquid phase, e.g. dip-coating or spray-coating. This allows to achieve additional functionalization such as a reduction in the coefficient of friction.

The substances intended for the coating, in particular oxides, nitrites, or oxynitrides of Si, Al, Ti, Zr, Hf, Y, Zn, can be applied using a sputter process from what is known as a sputter target, for example. It is possible for these materials to be provided in the form of metallic targets or as partially ceramic targets. The purity of the targets is typically specified to be 99% or more. However, lower purities are also possible. In this case, higher layer thicknesses might be necessary.

It can be envisaged to apply an adhesion layer or adhesion promoting layer on the lateral surface and/or a passivation layer on the reflector layer, preferably by cathode sputter deposition, high-frequency sputter deposition, reactive sputter deposition, magnetron sputter deposition, vapor deposition, in particular ion beam vapor deposition and/or thermal vapor deposition. In this case, the base layer portion may be provided so as to define an adhesion promoting layer. Accordingly, it may be envisaged to have greater adhesion between the base layer portion and the reflector layer applied thereto than would exist between a treated or non-treated lateral surface and a reflector layer applied thereto. In other words, increased adhesion can be provided between the reflector layer and the uppermost layer of the base layer portion therebelow, which may be in the form of a layer with increased surface energy and/or an increased number of oxygen radicals, or in the form of an adhesion layer deposited on the lateral surface by coating.

It is also possible for the base layer portion to consist of a plurality of adhesion layers, in which case at least one or each adhesion layer applied above the lowermost adhesion layer exhibits higher adhesion to the adhesion layer below than it would exhibit to the adhesion layer located below the adhesion layer below. In other words, the lateral surface or the optical element can be coated with a single or with multiple adhesion layers that define the base layer portion. For at least one adhesion layer it is intended to use at least one material selected from the group consisting of Si, Al, Ti, Zr, Hf, Y, or Zn, preferably in the form of an oxide, nitrite, or oxynitride. However, other substances may be used as well, for example boride, carbide, or carbonitride. Preferred layer systems include $TiO_2$, for example.

The base layer portion or the adhesion layer and/or the passivation layer can have an amorphous structure, but also a crystalline or polycrystalline structure, in particular if they include layer(s) applied by coating. Typical examples of amorphous coatings are $SiO_2$, $Si_3N_4$, $Al_2O_3$, AlSiOx, or BN, and typical examples of crystalline coatings are anatase or rutile $TiO_2$, $\gamma$-$Al_2O_3$, or crystalline AlN. However, it is in particular also possible to form mixed amorphous and crystalline phases.

For another preferred illumination system, a mirror layer or the reflector layer is envisaged to exhibit a different reflection behavior or transmission behavior for different wavelengths, in particular for wavelengths $\lambda_1$ and $\lambda_2$ that are close together, with a wavelength difference $\Delta\lambda = |\lambda_1 - \lambda_2| < 200$ nm, preferably <100 nm. This allows to implement an illumination system that can be switched over in terms of its emission characteristics, and these different wavelengths $\lambda_1$ and $\lambda_2$ can be set via the light source. The basic idea here is to design the reflector or mirror layer in such a way that for the first wavelength $\lambda_1$ the reflection layer applied to the lateral surface is largely transparent and transmissive for the radiation. In this way, the radiation behavior of a diffuser with emission all around can be achieved. When switching over to the second wavelength $\lambda_2$, the reflector layer on the side will then act as a mirror and will cause a directed emission laterally within a sector. For the two different wavelengths $\lambda 1$ and $\lambda 2$, the mirror layer or the reflector layer has preferably a different reflectivity and/or transmission of preferably at least 10%, more preferably at least 30%. This in particular makes it possible in an advantageous manner to achieve a significant change in the radiation between predominantly all-round radiation and focused radiation into a sector when switching the wavelength. The lateral reflector layer is therefore preferably designed to be rather narrow-band in terms of wavelength. In this case, it would be advantageous for the distal reflector to be highly reflective for both $\lambda_1$ and $\lambda_2$. This is in particular advantageous in medical technology applications of the illumination system. Examples of wavelengths $\lambda_1$ and $\lambda_2$ that are this close together would be the 980 nm and 1064 nm wavelengths which are often employed in medical technology applications. Such a behavior can be implemented in particular with the dielectric layer systems as described above. It should be noted here that $\lambda_1$ and $\lambda_2$ may of course also be further apart (>200 nm), which in medical applications can mean, however, that the absorption properties of the tissue may be very different for such diverging wavelengths. Therefore, the wavelengths can not be arbitrary and/or arbitrarily far apart.

In this context, another application can be mentioned, according to which different wavelengths that can in particular be switched over can be used to achieve different depths of penetration of the radiation, which can offer an advantage from a surgical point of view, in particular with regard to the penetration behavior in tissue.

The coating of the optical element with the reflector layer initially comprises the creation of a base layer portion consisting of a single adhesion layer and/or an activation of the lateral surface, or of a sequence of adhesion layers, and then the deposition (on the base layer portion) of a mirror layer consisting of a single layer or a sequence of in particular alternately high refractive index and low refractive index layers, or of a layer system of high-index and low-index layers. Activation of the lateral surface may refer to the removing of residues and/or the generation of an altered surface property, in particular increased surface energy and/or an increased number of oxygen radicals.

The coating or activation is preferably achieved at temperatures below 50° C. This relatively low temperature has the particular advantage that optical elements can be coated with a jacket in the form of a polymer layer. Furthermore preferred is processing in vacuum and in particular without vacuum interruption. Accordingly, it is possible, for example, to first produce the base layer portion in a vacuum, and to then apply the mirror layer in the same vacuum. Furthermore, the passivation layer may then be applied in the same vacuum.

A preferred use of the illumination system as described above in its various implementation variants is its use for photodynamic therapy (PDT) or photoimmunotherapy (PIT), for example for tumor treatment, for endovenous laser therapy (EVLT), for example for the treatment of varicose veins, for laser-induced interstitial thermotherapy (LITT) or for applications in the field of dental medicine, ophthalmology, and dermatology, as described in the introductory part. In the field of dental medicine, particular mention should be made of applications for treating wounds or periodontal disease. Furthermore, there are applications in brain research in which individual areas of the brain can be stimulated by light so as to treat disease symptoms.

Another application for the illumination system as described above in its various implementation variants is the use thereof in photodynamic therapy (PDT) or photoimmunotherapy (PIT) for tumor treatment, in which case at least one optical waveguide with the diffuser element captures light emitted from other diffuser elements, to forward it via the optical waveguide to a detector for spectroscopic analysis. In this case, light receiving diffuser optical waveguides are applied to the patient in addition to the diverse light emitting diffuser optical waveguides, and response to the PDT treatment can be assessed on the basis of the spectral differences between injected light and captured light (cf. Finlay et al., Proc. SPIE Int. Soc. Opt. Eng. 2014, June 14; 5315: Page 132-142). Furthermore, systems of this type can also be used for dosimetry, for example in PDT or PIT treatments.

In addition, applications in the industrial sector are also advantageous, for example as a component of a device for industrial applications for selectively illuminating cavities, for example for inspecting hard-to-reach places, for example on or in a machine, in which homogeneous illumination is particularly important, for illuminating through workpieces which have small openings, or else for spectroscopic applications, or in biochemistry where biochemical in vitro reactions are stimulated by light, i.e. for irradiation of samples in the context of in-vitro diagnostics. A further application can be seen in the selective curing of resins or adhesives or materials comprising such resins or adhesives, also where homogeneous illumination is needed or joints are difficult to access.

DESCRIPTION OF THE DRAWINGS

The invention will now be explained in more detail with reference to the accompanying figures. In the figures, the same reference symbols designate the same or equivalent elements, wherein.

DETAILED DESCRIPTION

In the following detailed description of embodiments, the same reference symbols in the accompanying figures denote the same or equivalent components. For better comprehension, definitions are provided as follows. For the purposes of the present disclosure, the term "illumination system" includes lighting devices and in particular lighting devices which are suitable for use for medical technology purposes and which can be disinfected and/or sterilized at least in sections thereof, in particular insofar as they are intended to come into contact with living tissue. The wording "for a medical technology therapy and/or diagnosis system" in particular also encompasses the suitability, use, or application of the presently disclosed illumination system itself as a medical therapy and/or diagnosis system, without being limited thereto.

Figure 1:
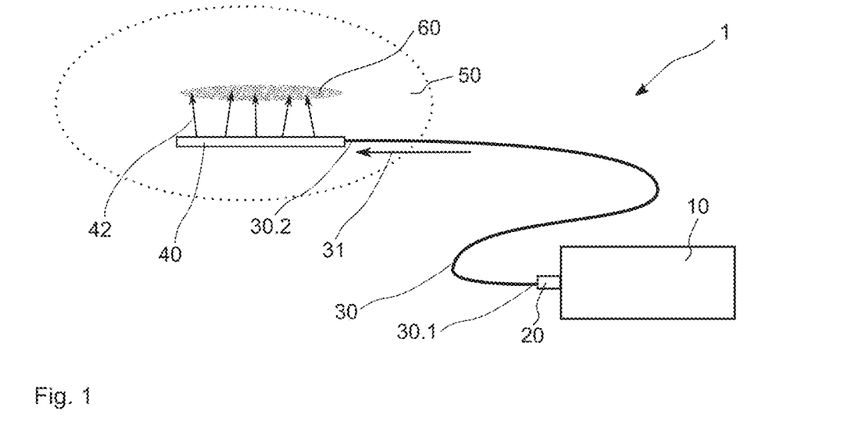
FIG. 1 is a schematic view of an illumination system comprising an optical waveguide and a diffuser element that emits from a section thereof in one direction, in a PDT or PIT application.

FIG. 1 schematically shows the configuration of an illumination system 1 according to the invention. By way of example, a medical PDT application is illustrated. In the illustrated example, the illumination system 1 comprises an LED or laser light source 10 which emits light in a specific spectral range in its operating state. For PDT or PIT applications as described in the introductory part, lasers are used which emit at a wavelength that is matched to the previously administered biochemically modified dye (photosensitizer), usually in the visible range, for example in the green spectral range at 532 nm, or in the red spectral range, for example at 690 nm.

An optical waveguide 30 is connected to the laser light source 10 at its proximal end 30.1, by a plug-in connector 20 or other coupling or connection element. Here, proximal end 30.1 refers to the end of the optical waveguide 30 into which light is injected. At its distal end 30.2, the optical waveguide 30 has an optical element in the form of a diffuser element 40 which is introduced into or close to a tumor tissue 60 that has formed inside of and therefore adjoins a healthy tissue 50. Here, distal end 30.2 refers to the other end of the optical waveguide 30, which is usually located remote of the proximal end 30.1 of optical waveguide 30 and from which in particular light is emitted.

The laser radiation reaches the diffuser element 40 through light injection 31 via the optical waveguide 30 provided on the diffuser element 40 which is defined by a diffuser base body 41, for example. The light is emitted laterally over the length of the diffuser element, which is defined by the longitudinal axis L, or is emitted from the light-transmissive area, as light emission 42. What is important here is that the emission over the length of the diffuser element 40 is as homogeneous as possible. In particular intensity peaks should be avoided. In the illustrated example, the diffuser element 40 only emits in one direction, i.e. section-wise, into the tumor tissue 60. A photo-induced biochemical reaction as described in the introductory part will ideally induce necrosis of the tumor tissue 60 after the treatment.

Without being limited to the example shown here, fused silica fibers are usually employed as the optical waveguides 30, and the plug-in connectors 20 are usually in the form of coaxial connectors known as SMA connectors which preferably have the fibers glued into the connector 20. With regard to thermal load capacity, plug-in connectors 20 with nickel silver sleeves may furthermore be advantageous, in which the optical waveguide 30 is accommodated in the nickel silver sleeve with a positive fit, in particular by plastic deformation, e.g. crimped. Moreover, for higher laser output powers it is also possible to use plug-in connectors 20 in which the fiber end of the optical waveguide 30 is protected by a conical prism, which can be advantageous in the case of incorrect adjustments.

Figure 2:
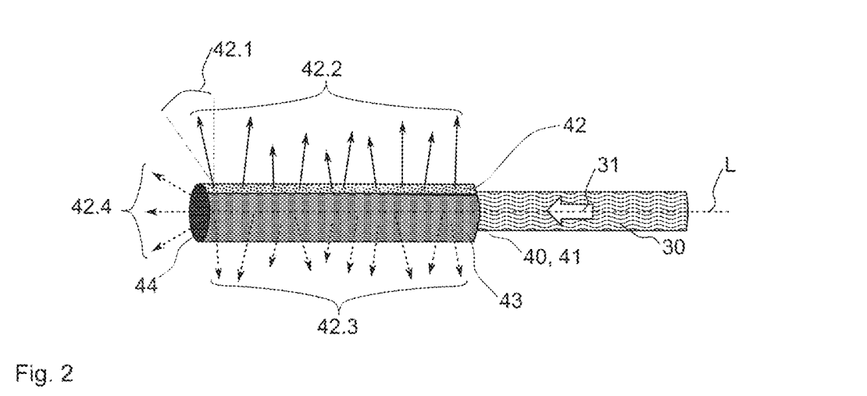
FIG. 2 is a schematic view of a diffuser element.

FIG. 2 schematically shows the configuration of the diffuser element 40, by way of example. Diffuser element 40 consists of a diffuser base body 41 which is preferably spliced or glued to the optical waveguide 30. In the applications described above, the optical waveguide 30 is mostly made of fused silica and comprises a core. The core has a refractive index $n_1$ and a core diameter of usually between 100 µm and 1000 µm, preferably between 200 µm and 600 µm, and a cladding or cladding surface that has a refractive index $n_2$, with $n_1 > n_2$. Usually, a numerical aperture NA of approximately 0.22 or less, for example 0.1, can be achieved in this way. It is also possible to achieve higher NA values of up to 0.4 or 0.6, with special doping. Light injection 31 from the optical waveguide 30 occurs via a respective injection surface of the diffuser base body 41.

Furthermore, in the case of a spliced connection it can be advantageous for the connection between diffuser base body 41 and optical waveguide 30 to be implemented in two steps. First, only a short portion (typically a few 10 mm long, e.g. approx. 10 to 20 mm) of the optical waveguide 30 is spliced to the diffuser base body 41, which is then coated, and subsequently the actual pigtail consisting of optical waveguide 30 and plug-in connector 20 is spliced to the short portion of optical waveguide 30. This is particularly advantageous since the reflector coating will not be thermally destroyed or the reflection properties will not be inadmissibly altered by the splicing process during which high local energy density is induced by laser and/or corona discharges. Moreover, the diffuser base body 41 with merely the short portion of optical waveguide 30 is installed more easily in the coating chamber during the coating process. Handling effort can thus be significantly reduced compared to the handling with a complete pigtail.

The diffuser base body 41 or the optical element comprises, for example, a matrix of matrix elements with embedded scattering elements and/or a jacket tube. However, the diffuser base body 41 may also be made of a glass whose scattering properties can be selectively adjusted by thermal treatment under predefined temperature-time control. Also conceivable for the diffuser base body 41 is a matrix made of a glass ceramic in which it is also possible to selectively adjust the crystallite density and/or the size of the crystallites by a selective temperature-time treatment so that the scattering property can be influenced here as well. Also conceivable are optical elements based on plastics material, in which case a polymer optical fiber (POF) will be attached as the optical waveguide 30.

A sleeve made of plastics, glass, metal, or ceramic material may be provided in order to avoid stray light from the bonding zone between optical waveguide 30 and diffuser base body 41, but also as a mechanical stabilization of this bonding zone.

The diffuser element 40 has a reflector layer 43 and optionally also a reflector or a further reflector layer at the distal end 44. This results in essentially 3 contributions to light emission 42: lateral light emission 42.2 with a pre-definable emission angle 42.1, rear-side light emission 42.3 through the reflector layer, and distal light emission 42.4.

For a medical technology application in which tissue is to be irradiated in a targeted manner, the proportion of rear-side light emission 42.3 should therefore be as small as possible, which makes it necessary for the reflector layer 43 to have the highest possible reflectance. In addition, it may also be necessary to largely prevent distal light emission 42.4 at the distal end 44, which in this case also implies the highest possible reflectance of the reflector layer at the distal end 44. Moreover, a highest possible reflectance at the distal end 44 provides for increased back reflection and thus increased efficiency of lateral light emission 42.2. In both cases, reflectance values of more than 90%, preferably more than 95%, and most preferably more than 99% are required. In addition, the reflector layer must not exhibit large absorption in order to prevent excessive heating.

Corrosion resistance is also important, in particular with regard to complex cleaning processes and mechanical loads, for example when the diffuser element 40 is repeatedly moved inside a catheter, which causes friction. The applied layers of the reflector coating can therefore be subjected to cleaning processes (e.g. with ethanol) or even pass abrasion tests, for example the rubber test or the self-adhesive tape test also known as "Tesa test", or the TABER test.

Figure 3:
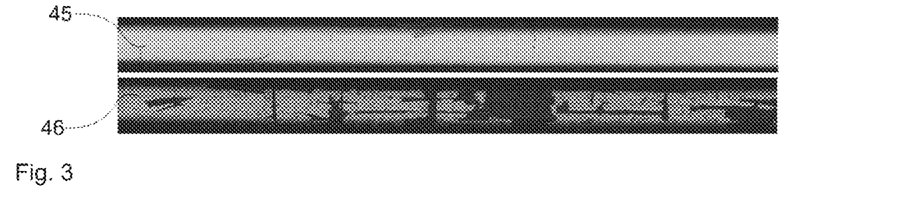
FIG. 3 shows a comparison of the differently coated surfaces after an abrasion test.

FIG. 3 therefore shows a comparison after a rubber test: the top of the picture shows the reflector layer 43 in the form of a dielectric multilayer system 45 with a 4-layer design. For comparison, the bottom picture shows the surface of a metallic Cr+Au reflector coating 46. As can be seen, a purely metallic reflector coating does not adequately withstand the loads, and a dielectric multi-layer system 45 can be better matched with regard to the mechanical load capacity.

Figure 4:
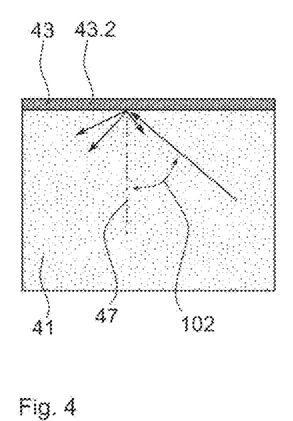
FIG. 4 is a schematic view of an exemplary embodiment of a reflector layer.
Figure 5:
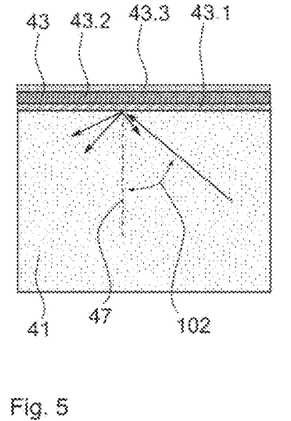
FIG. 5 is a schematic view of an exemplary embodiment including a reflector layer, an adhesion layer, and a passivation layer.
Figure 6:
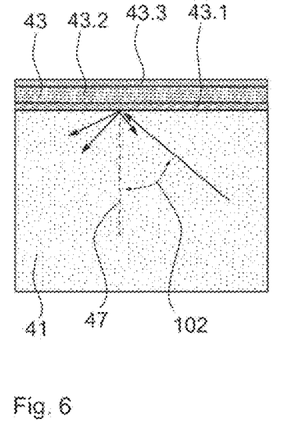
FIG. 6 is a schematic view of an exemplary embodiment including a dielectric reflector layer, an adhesion layer, and a passivation layer.

FIGS. 4 to 6 schematically illustrate typical exemplary embodiments of the reflector layer 43, not shown to scale. FIG. 4 shows a simple layer structure for the lateral surface reflector 43, comprising a metallic mirror layer 43.2 that has been deposited on the diffuser base body 41. The light to be reflected can be incident on the mirror layer 43.2, on the adhesion promoting layer 43.1, or on the reflector layer 43 at different angles of incidence 102 relative to the perpendicular 47, here.

Advantageously, for light that is incident at an angle to the reflector surface, maximum reflectance is greater than 50%, preferably greater than 70%, and most preferably greater than 90%. In the context of the present disclosure, light incident at an angle is understood to mean that the light is incident on the reflector layer 43 at an angle between absolutely 0° and up to 90°, or preferably at an angle of more than 50°, preferably more than 70° to the perpendicular 47 of the reflector layer 43. Since the light is substantially conducted and scattered longitudinally of the diffuser element 41, a certain percentage of the light will be incident on the reflector layer 43 at an angle. It is therefore advantageous if this portion of the light is also reflected.

Metallic mirror layers 43.2 can preferably be made of noble metals such as Au, Ag, Pd, or Pt, which exhibit high reflectance in the visible range of light. Also conceivable are alloys of several metals or multi-layered metal layers. However, as shown in FIG. 3, such layers with a simple structure may in some cases not be practical with regard to mechanical abrasion, adhesion, or chemical attack.

FIG. 5 therefore shows a more complex, multi-layered structure comprising an adhesion layer 43.1 or adhesion promoting layer directly on the diffuser base body 41, the actual mirror layer 43.2, and an additional passivation layer 43.3. It should be noted here that the conventional adhesion promoters for noble metals, such as Cr or Ni, lead to a reduction in reflectivity, since the light is guided through the fiber or the optical element. This is true even in the case of very small layer thicknesses of the adhesion layer 43.1 of 10 nm, for example. Dielectric layers can be used as alternative adhesion layers 43.1 in order to not reduce reflectivity significantly. Here, oxides, nitrides, or oxynitrides of Si, Al, Si, Al, Ti, Zr, Hf can be used, and optionally also Y and Zn. The noble metal layers defining the mirror layer 43.2 may have a thickness ranging between 10 nm and 5000 nm, preferably in the range between 10 nm and 300 nm. The adhesion layer 43.1 or adhesion promoting layer typically has a thickness of a few tens of nanometers at most, preferably in the range from 5 nm to 50 nm.

Another example of a possible mirror layer 43.2 is a base metal layer with high reflectivity, for example comprising Mg, Al, or Cu, embedded in an optical design so as to enhance reflectivity. In its simplest form, a 3-layer design of $TiO_2$(Mg), $SiO_2$, and Mg is produced, in which case the reflectivity of the metal layer can be increased by using a high-index first layer, a low-index second layer, and a highly reflective metal layer for increasing reflectivity. A further layer, in particular a passivation layer 43.3 following the metal layer, ensures additional protection against corrosion. This additional barrier layer/passivation layer may comprise oxides, nitrides, or oxynitrides of Si, AlSi, Al, Ti, Zr, Hf, and optionally also Y and Zn. The optical specifications of the layer are not relevant at this location, which is why sacrificial metal layers could also be used, which corrode instead of the functional metal layer. These may include Al, Cu, Cr, or Ni, for example. But other metals are conceivable as well.

By way of example and without being limited to the values presented, Example 1 below gives the layer thicknesses of a functional 3-layer system of a reflector layer 43, which are in the following ranges: $TiO_2$ (as an adhesion layer 43.1): ranging from 30 nm to 5000 nm, preferably between 30 nm and 300 nm, typically 100 nm to 200 nm. $SiO_2$: ranging from 40 nm to 5000 nm, preferably between 40 nm and 380 nm, typically 150 nm to 250 nm. Mg: ranging from 20 nm to 2000 nm, preferably between 20 nm and 200 nm, typically 50 nm to 150 nm. $SiO_2$: ranging from 5 nm to 5000 nm, preferably between 5 nm and 500 nm, typically 100 nm to 250 nm.

The presented design allows to increase the reflectance in a wavelength range above 1000 nm to more than 90%, preferably to more than 92%, or preferably even to more than 95%, in particular for light that is incident perpendicular to the reflector layer 43. Furthermore, the layer system is distinguished by the fact that high reflectance is retained in an angular range from 0 to +/−80°, measured relative to the perpendicular of the reflector layer 43, which is necessary for the intended application in the medical field, in particular for irradiation of tissue. For the purposes of the invention, high reflectance is understood to mean a reflectance of more than 50%, preferably more than 70%, more preferably more than 90% in an angular range as specified above around the maximum reflectance for perpendicular incidence of light.

A significant advantage of a Mg-based layer according to Example 1 is the high reflectance of a base metal coating, similar to that of Cu or Al. A major advantage of this variant is that it is easy to manufacture. Since only a few layers are necessary, these can also be produced in large systems or in-line systems. Furthermore, there are no major requirements for uniformity in this case. Moreover, $TiO_2$ and $SiO_2$ layers are easy to master, as these are standard processes. Also, an Mg layer as a metallic layer is easy to produce. Another advantage over softer noble metal layers is the good adhesion and mechanical resistance. The applied layers can be subjected to cleaning processes (e.g. with ethanol) or even pass abrasion tests, as shown in FIG. 3.

FIG. 6, similar to FIGS. 4 and 5, shows a further example in the form of an interference-optical dielectric system. Here, the mirror layer 43.2 is composed of alternate high refractive index and low refractive index layers, so that high reflectance can be achieved on the basis of transparent dielectric layers, in accordance with Fresnel's relations. This is achieved by adjusting the quarter wave layer thickness for a reference wavelength. Materials that can be considered for this approach include $TiO_2$, $Ta_2O_5$, $Nb_2O_5$, or $ZrO_2$ as high-index layers or, more generally, as layers with a refractive index of more than 2.2. The materials mentioned can furthermore be stabilized by doping, such as by Al, Si, Y, Zn. In particular $SiO_2$ or doped $SiO_2$ variants can be considered for the low-index layer. Oxides, nitrides, fluorides (e.g. $MgF_2$) or oxynitrides of other metals are also possible. $SiO_2$ with low $N_2$ doping is also conceivable and very well meets the requirement of a low refractive index of preferably less than 1.5. With such designs it is possible to obtain broadband and highly reflective reflector layers 43 or mirror layers 43.2, for example with a high-index and low-index layer system made up of 11 layers, for example with layer thicknesses for $TiO_2$ between 120 nm and 130 nm, and for $SiO_2$ between 210 nm and 220 nm, in particular for a wavelength range between 1000 nm and 1100 nm. Due to the broadband nature, different angles of incidence in a wide range can be reflected for a predefined reference wavelength (here for example for 1064 nm).

Figure 7:
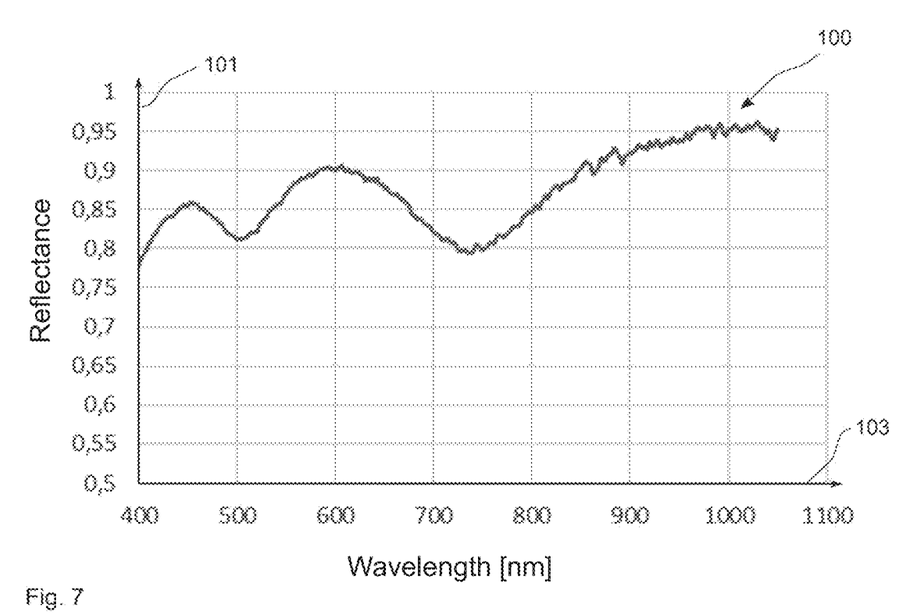
FIG. 7 is a graph showing a reflectance curve as a function of wavelength.

FIG. 7 shows a graph 100 with a profile of reflectivity 101, i.e. reflectance, as a function of wavelength 103 for a multi-layered system consisting of $TiO_2/SiO_2/Mg/SiO_2$ as described in Example 1. With such a system, reflectance is particularly high, e.g. more than 90%, at wavelengths around 600 nm and in the wavelength range from approximately 900 nm to approximately 1100 nm.

Figure 8:
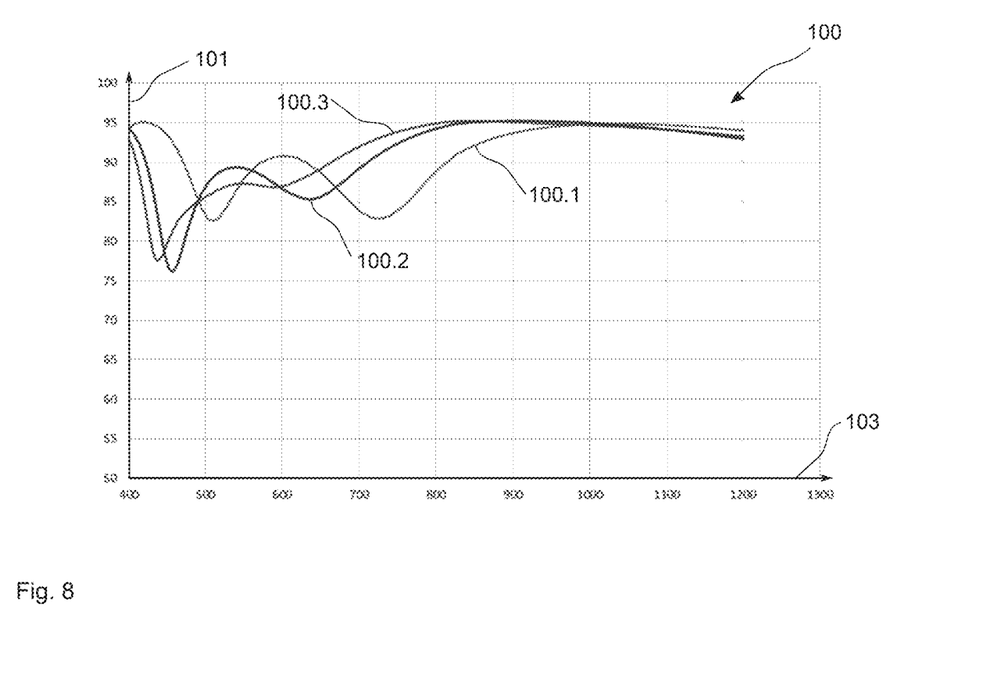
FIG. 8 is a graph showing reflectance curves as a function of wavelength for different light incidence angles.

FIG. 8 shows another graph 100 with profiles of reflectivity 101, i.e. reflectance, as a function of wavelength 103 for the layer system illustrated in FIG. 7 for different angles of incidence 102. The first curve, 100.1, is a profile for an angle of incidence to the vertical of 0°. The second curve, 100.2, was measured for an angle of incidence of 60° relative to the vertical, and the third curve, 100.3, was measured for an angle of incidence of 80° relative to the vertical. As can be seen here, a reflectance value of 95%, almost independent of the angle, can be achieved in a range from 1000 nm to 1100 nm, for example. In the illustrated example, such a layer system was optimized for an application wavelength of 1064 nm. By varying the individual thicknesses of the layers of mirror layer 34.2 it is possible to adjust such a high, almost angle-independent reflectance for a wide range of wavelengths.

Figure 9:
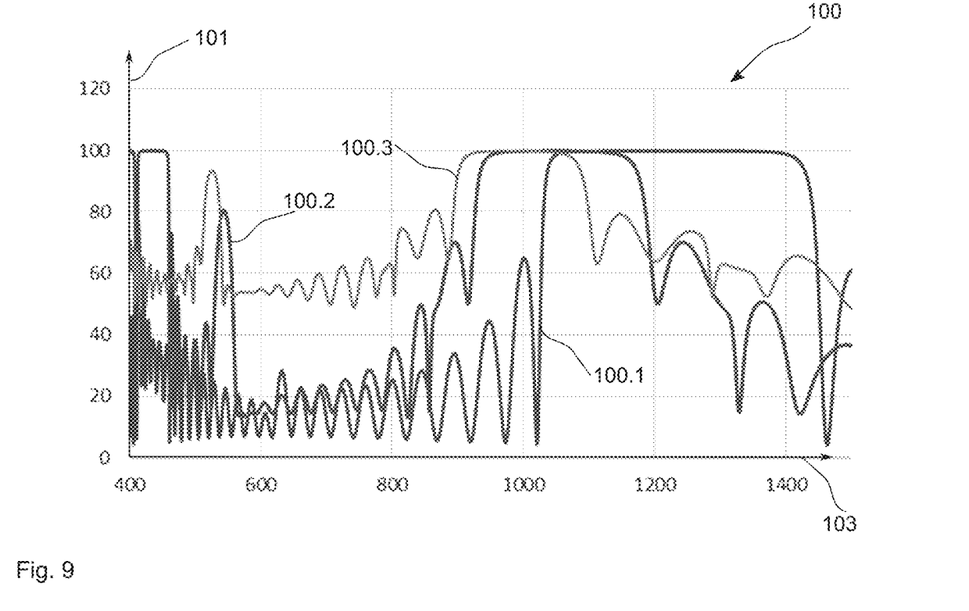
FIG. 9 is a graph showing reflectance curves as a function of wavelength and for different angles of incidence for an interference reflector.

FIG. 9 shows another graph 100 with different profiles 100.1, 100.2, 100.3 of reflectance 101 for different angles of incidence 102, in particular for a 11-layer high-index and low-index layer design consisting of $TiO_2/SiO_2$, here with the maximum value normalized to 100%. The first curve, 100.1, represents the 0° angle of incidence 102, the second curve, 100.2, represents the 60° angle of incidence 102, and the third curve, 100.3, represents the 80° angle of incidence 102 relative to the perpendicular to mirror layer 43.2. The center wavelength is approx. 1040 nm to 1060 nm in this case.

Such layer variants allow to achieve very highly reflective designs, depending on the absorption or haze of the employed layers. The absorption depends on the employed materials and the manufacturing process, haze can be caused by the cleanliness of the substrates, defects in the coating process, plasma polymerization, crack formation, or the like. Since a coating process must be extremely reproducible and stable, PVD-based processes such as vapor deposition or sputter deposition, e.g. magnetron sputter deposition or ion beam sputter deposition, are preferably employed to produce the reflector layer 43, adhesion layer 43.1, and/or the passivation layer 43.3.

The coating process can be implemented using a magnetron sputter deposition process, for example. In this case, the process for a 3- or 4-layer system comprises the steps of: cleaning the substrate surface or lateral surface or the surface of the optical element using an ultrasonic cleaning process; thermal treatment of the lateral surface or surface of the optical element in vacuum to improve adhesion by dehydration of the surface; reactive magnetron sputter deposition of the $TiO_2$ and $SiO_2$ layers from the metallic target, or sputter deposition of $TiO_2$ from the ceramic target, and metallic sputter deposition of Mg; Defect-free sputter deposition, for example by arranging the system and substrate or by arranging the optical element vertically.

In a further step, in particular an additional process step, oxygen plasma pretreatment can be performed in vacuum. This is intended to improve adhesion by preconditioning the surface. However, plasma pretreatments in particular under atmospheric pressure are also advantageous.

In the case of metallic layers as the reflector layer, it is also conceivable that these layers are first applied to a preform of the diffuser blank, and subsequently the diffuser is drawn in a drawing process.

LIST OF REFERENCE SYMBOLS

1 Illumination system
10 Laser light source
20 Plug-in connector
30 Optical waveguide
30.1 Proximal end of optical waveguide
30.2 Distal end of optical waveguide
31 Light injection
40 Diffuser element
41 Diffuser base body
42 Light emission from light-transmissive area
42.1 Radiation angle
42.2 Lateral light emission
42.3 Rear light emission
42.4 Distal light emission
43 Reflector layer (light-reflecting area)
43.1 Adhesion layer
43.2 Mirror layer
43.3 Passivation layer
44 Distal end of reflector
45 Dielectric multilayer system
46 Metallic reflector coating
47 Vertical
50 Tissue
60 Tumor tissue
100 Profile chart
100.1 $1^{st}$ profile
100.2 $2^{nd}$ profile
100.3 $3^{rd}$ profile
101 Reflectance
102 Angle of incidence
103 Wavelength
L Longitudinal axis

What is claimed is:

1. An illumination system for a medical technology therapy and/or diagnosis system, comprising:
   a light source;
   an optical waveguide having a proximate end and a distal end, the proximal end is connectable or assignable to the light source; and
   an optical element arranged at the distal end so that light from the optical waveguide is injected into the optical element, the optical element defining a longitudinal axis (L) and having a lateral surface extending around the longitudinal axis, wherein the lateral surface is at least in a section covered by a reflector layer,
   wherein the reflector layer comprises a mirror layer and the optical element comprises a light-reflecting area covered by the reflector layer, the optical element further comprising a light-transmissive area that remains free of the reflector layer so that the light injected into the optical element is reflected at the light-reflecting area and is emitted from the light-transmissive area,
   wherein the reflector layer exhibits a reflectance of more than 90% for at least one wavelength range.

2. The illumination system of claim 1, wherein the optical element is a diffuser element.

3. The illumination system of claim 1, wherein the optical element is configured to emit light transversely to the longitudinal axis (L) of the optical element and laterally over an active length of the optical element.

4. The illumination system of claim 1, further comprising a maximum reflectance of greater than 95% for perpendicular incidence of light to the reflector layer, wherein the reflectance is selectively adjustable to a predefined wavelength of the light or in a predetermined range around a main wavelength of the light.

5. The illumination system of claim 1, wherein, for a light incidence angle of greater than 45° with respect to a perpendicular to the reflector layer, the reflectance of the reflector layer is more than 50% of the reflectance at perpendicular incidence of light.

6. The illumination system of claim 1, wherein, for a light incidence angle of greater than 80° with respect to a perpendicular to the reflector layer, the reflectance of the reflector layer is more than 90% of the reflectance at perpendicular incidence of light.

7. The illumination system of claim 1, wherein the diffuser element has an area not covered by the reflector layer, wherein the area extends along the longitudinal extension of the diffuser element and is light-transmissive so that light carried through the diffuser element is emitted in a strip-like shape.

8. The illumination system of claim 1, wherein the mirror layer comprises or is made of a metallic layer having a metal selected from a group consisting of noble metals, Mg, Al, Cu, and combinations thereof.

9. The illumination system of claim 1, wherein the reflector layer further comprises a feature selected from a group consisting of: a lower layer disposed below the mirror layer, an upper layer disposed above the mirror layer, an adhesion layer disposed below the mirror layer, an adhesion promoting layer disposed below the mirror layer, a layer portion on the diffuser base body that has chemically and/or physically modified surface properties, a layer on the optical element that has a chemically and/or physically modified surface property, and a near surface zone of the optical element that has a chemically and/or physically modified surface property.

10. The illumination system of claim 1, wherein the mirror layer or the reflector layer comprise scattering centers or comprises a layer that comprises scattering centers, wherein the light is reflected diffusely at the scattering centers.

11. The illumination system of claim 10, wherein the mirror layer or the reflector layer comprise a metal or a chemical metal compound, wherein the light is reflected in a directed manner on the metal or chemical metal compound.

12. The illumination system of claim 1, wherein the reflector layer is arranged at the distal end of the diffuser element and/or at least partially encloses the diffuser element laterally.

13. The illumination system of claim 1, wherein the diffuser element comprises scattering elements in a matrix of the diffuser element, and/or wherein the matrix of the diffuser element is laterally enclosed by a material that includes scattering elements.

14. The illumination system of claim 1, wherein the scattering elements comprise white glass rods enclosed by a cladding tube made of borosilicate glass.

15. The illumination system of claim 1, wherein the diffuser element comprises glass selected from a group consisting of: borosilicate glass, phosphate crown glass, lead silicate glass, tin silicate glass, and alkali zinc glass.

16. The illumination system of claim 1,
wherein the diffuser element is structured at least partially or in sections of a volume and/or a surface; or
wherein the diffuser element comprises a jacket formed of a material selected from a group consisting of: colored glass, colorless glass, transparent glass, and colored plastics material.

17. The illumination system of claim 1, wherein the illumination system is configured for a use selected from a group consisting of: a component of a device for a medical therapy method, a component of a device for photodynamic therapy (PDT), a component of a device for photoimmunotherapy (PIT) for tumor treatment, a component of a device for endovenous laser therapy (EVLT) for the treatment of varicose veins, a component of a device for laser-induced interstitial thermal therapy (LITT), a component of a device for dental medicine, a component of a device for ophthalmology, a component of a device for dermatology, a component of a device for selective illumination of cavities, and a component of a device for irradiation of in-vitro diagnostic samples.

18. An illumination system for a medical technology therapy and/or diagnosis system, comprising:
a light source;
an optical waveguide having a proximate end and a distal end, the proximal end is connectable or assignable to the light source; and
an optical element arranged at the distal end so that light from the optical waveguide is injected into the optical element, the optical element having a lateral surface with at least in a section that is covered by a reflector layer,
wherein the reflector layer comprises a mirror layer and the optical element comprises a light-reflecting area covered by the reflector layer, the optical element further comprising a light-transmissive area that remains free of the reflector layer so that the light injected into the optical element is reflected at the light-reflecting area and is emitted from the light-transmissive area, wherein the reflector layer exhibits a reflectance of more than 90% for at least one wavelength range, and
wherein the reflector layer further comprises a dielectric layer disposed above and/or below the mirror layer, the dielectric layer comprising oxides, nitrides, or oxynitrides of at least one element selected from a group consisting of Si, Al, Ti, Zr, Hf, Y, and Zn.

19. An illumination system for a medical technology therapy and/or diagnosis system, comprising:
a light source;
an optical waveguide having a proximate end and a distal end, the proximal end is connectable or assignable to the light source; and
an optical element arranged at the distal end so that light from the optical waveguide is injected into the optical element, the optical element having a lateral surface with at least in a section that is covered by a reflector layer,
wherein the reflector layer comprises a mirror layer and the optical element comprises a light-reflecting area covered by the reflector layer, the optical element further comprising a light-transmissive area that remains free of the reflector layer so that the light injected into the optical element is reflected at the light-reflecting area and is emitted from the light-transmissive area, wherein the reflector layer exhibits a reflectance of more than 90% for at least one wavelength range, and
wherein the mirror layer or the reflector layer is a dielectric multilayer system comprising a sequence of low-index and high-index metal oxides and/or metal nitrides.

20. A method for producing an illumination system for a medical technology therapy and/or diagnosis system, for use on living tissue, comprising:
connecting or assigning a light source to a proximal end of an optical waveguide;
providing an optical element in the form of a diffuser element defining a longitudinal axis and having a lateral surface extending around the longitudinal axis;
arranging the optical element at a distal end of the optical waveguide so that light from the optical waveguide is injected into the optical element; and
covering at least part of the lateral surface with a light-reflecting reflector layer so that the optical element comprises a light-reflecting area that is covered by the reflector layer and a light-transmissive area that remains free of the reflector layer so that light to be emitted by the optical element is at least partially reflected and light is selectively emitted from the light-transmissive area, wherein the reflector layer exhibits a reflectance of more than 90% for at least one wavelength range.

* * * * *